United States Patent [19]
Forestier et al.

[11] Patent Number: 5,863,522
[45] Date of Patent: Jan. 26, 1999

[54] SCREENING COSMETIC COMPOSITION COMPRISING ONE NANOPIGMENT OF METALLIC OXIDE AND ONE FAT-SOLUBLE SCREENING POLYMER

[75] Inventors: Serge Forestier, Claye-Souilly; Isabelle Hansenne, Paris, both of France

[73] Assignee: L'Oreal, Paris, France

[21] Appl. No.: 895,865

[22] Filed: Jul. 17, 1997

Related U.S. Application Data

[62] Division of Ser. No. 39,324, filed as PCT/FR92/00821, Aug. 25, 1992, Pat. No. 5,733,895.

[30] Foreign Application Priority Data

Aug. 29, 1991 [FR] France .................................. 91/10731

[51] Int. Cl.$^6$ .......................... A61K 7/42; A61K 31/695
[52] U.S. Cl. ............................... 424/59; 424/60; 424/63; 424/70; 424/81
[58] Field of Search ................................ 424/59, 60, 63, 424/70, 81, 401

[56] References Cited

U.S. PATENT DOCUMENTS

| | | | |
|---|---|---|---|
| 4,839,160 | 6/1989 | Forestier et al. | 424/59 |
| 5,000,937 | 3/1991 | Grollier et al. | 424/47 |
| 5,061,479 | 10/1991 | Grollier et al. | 424/47 |
| 5,087,445 | 2/1992 | Haffey et al. | 424/59 |
| 5,099,027 | 3/1992 | Vogl et al. | 548/259 |
| 5,207,998 | 5/1993 | Robinson et al. | 424/59 |
| 5,215,749 | 6/1993 | Nicoll et al. | 424/401 |
| 5,250,289 | 10/1993 | Boothroyd et al. | 424/59 |
| 5,695,747 | 12/1997 | Forestier et al. | 424/59 |

FOREIGN PATENT DOCUMENTS 2 657 351  7/1991  France .
WO 90/11067  10/1990  WIPO .

*Primary Examiner*—Ceila Chang
*Attorney, Agent, or Firm*—Jacobson, Price, Holman & Stern, PLLC

[57] ABSTRACT

The present invention is directed to a composition for screening out ultraviolet radiation, comprising, in association, at least one nanopigment of metallic oxide and at least one UV-screening fat-soluble polymer.

15 Claims, No Drawings

5,863,522

SCREENING COSMETIC COMPOSITION COMPRISING ONE NANOPIGMENT OF METALLIC OXIDE AND ONE FAT-SOLUBLE SCREENING POLYMER

This is a divisional application of application Ser. No. 08/039,324, filed Apr. 23, 1993, now U.S. Pat. No. 5,733,895 which is a 371 of PCT/FR92/00821, filed Aug. 25, 1992.

The subject of the present invention is a composition for screening out ultraviolet radiation, comprising, in association, at least one nanopigment of metallic oxide and at least one UV-screening fat-soluble polymer.

It is known that light radiation with wavelengths of between 280 and 400 nm permit the tanning of the human epidermis and that rays with wavelengths of between 280 and 320 nm, known by the name UV-B, also cause erythemas and skin burns which can hamper the development of the tan.

However, while UV-B rays with wavelengths of between 280 and 320 nm play a preponderant part in the production of solar erythema and must be screened out, it is nevertheless a fact that UV-A rays with wavelengths of between 320 and 400 nm which cause tanning of the skin are also capable of inducing its degradation especially in the case of a sensitive skin or a skin continuously exposed to solar radiation. UV-A rays cause in particular a loss of elasticity of the skin and the appearance of wrinkles which result in early ageing. They promote the onset of the erythemal reaction or amplify this reaction in certain subjects and may even be responsible for phototoxic or photoallergic reactions.

Compounds are known which have the property of absorbing ultraviolet radiation in the erythemal region while allowing the radiation responsible for tanning to pass through and it has already been proposed to use such compounds as "sunscreen" agents in cosmetic compositions which promote the acquisition of skin tan while avoiding skin burns and irritations.

Synthetic or natural carbon-containing polymers and siloxane polymers carrying an ultraviolet-absorbing group are also known which possess the advantage of reducing or even suppressing the penetration of the screening compound into the body.

Metallic oxides such as titanium oxide are useful because of their ultraviolet ray diffusion and reflection properties over a broad band. However, the effectiveness of the cosmetic compositions containing only metallic oxides, expressed by the solar protection factor which is generally called "protection index" or PI, is inadequate for very sensitive skins or skins continuously exposed to solar radiation, especially with respect to the UV-B protection index.

The protection index or PI may be expressed by the ratio of the irradiation time required to reach the erythematogenic threshold with the UV-screening agent to the time required to reach the erythematogenic threshold without a UV-screening agent.

Cosmetic compositions containing only "screening polymers" have the same disadvantage.

In the following text, a polymer of hydrocarbon or siloxane structure, carrying at least one ultraviolet-absorbing group, will be called "screening polymer".

Moreover, at the industrial level, it is of course advantageous to have UV-screening agents which make it possible, at low concentrations, to obtain anti-sun compositions with a high protection index.

The Applicant has just discovered that by combining at least one nanopigment of metallic oxide, having a particle size less than 100 nm, with at least one fat-soluble screening polymer, in a cosmetically acceptable carrier, there was surprisingly obtained, for a composition containing a given concentration of the nanopigment and the screening polymer taken together, a protection index, especially a UV-B protection index, substantially greater than the protection indices of compositions containing either a nanopigment, or a screening polymer, at the same concentration and in the same carrier.

The subject of the present invention is therefore a cosmetic composition for screening out ultraviolet radiation with wavelengths of between 280 and 400 nm, which contains at least one nanopigment of metallic oxide and at least one screening polymer chosen from fat-soluble polymers with a hydrocarbon structure and polymers with a siloxane structure, in a cosmetically acceptable carrier.

The subject of the present invention is also a process for protecting the human epidermis and the hair against ultraviolet radiation with wavelengths of between 280 and 400 nm, which consists in applying to the skin an effective amount of the abovementioned screening cosmetic composition comprising, in association, at least one nanopigment of metallic oxide and at least one fat-soluble screening polymer.

The pigments of metallic oxides are chosen from titanium, zinc, cerium, zirconium or iron oxides or mixtures thereof. In the present application, "nanopigments" are understood to mean pigments with a mean diameter of less than 100 nanometers, preferably of between 5 and 50 nanometers. These nanopigments may be coated or uncoated.

The coated pigments are pigments which have undergone one or more surface treatments of a chemical, electronic, mechanicochemical and/or mechanical nature with compounds, as described for example in Cosmetics & Toiletries, February 1990, Vol. 105, p. 53–64, such as amino acids, beeswax, fatty acids, fatty alcohols, anionic surfactants, lecithins, sodium, potassium, zinc, iron or aluminum salts of fatty acids, metallic alkoxides (of titanium or aluminum), polyethylene, silicones, proteins (collagen, elastin), alkanolamines, silicon oxides, metallic oxides or sodium hexametaphosphate.

The coated pigments are more particularly titanium oxides coated:

with silica, such as the product "SUNVEIL" from the company IKEDA, with silica and iron oxide, such as the product "SUNVEIL F" from the company IKEDA, with silica and alumina, such as the products "MICROTITANIUM DIOXIDE MT 500 SA" and "MICROTITANIUM DIOXIDE MT 100 SA" from the company TAYCA, "TIOVEIL" from the company TIOXIDE, with alumina, such as the products "TIPAQUE TTO-55(B)" and "TIPAQUE TTO-55(A)", from the company ISHIHARA, and "UVT 14/4" from the company KEMIRA, with alumina and aluminum stearate, such as the product "MICROTITANIUM DIOXIDE MT 100 T" from the company TAYCA, with alumina and aluminum laurate, such as the product "MICROTITANIUM DIOXIDE MT 100 S" from the company TAYCA, with iron oxide and iron stearate, such as the product "MICROTITANIUM DIOXIDE MT 100 F" from the company TAYCA, with zinc oxide and zinc stearate such as the product "BR 351" from the company TAYCA, with silica, alumina and silicone, such as the products "MICROTITANIUM DIOXIDE MT 600 SAS" and "MICROTITANIUM DIOXIDE MT 500 SAS" from the company TAYCA, with silica, alumina, aluminum stearate and silicone, such as the product "STT-30-D-S" from the company TITAN KOGYO, with alumina and silicone, such as the product "TIPAQUE TTO-55(S)" from the company ISHIHARA, with triethanolamine, such as the product "STT-65-S" from the company TITAN KOGYO, with stearic acid such as the product "TIPAQUE TTO-55 (C)" from the company ISHIHARA, with sodium hexametaphosphate, such as the product "MICROTITANIUM DIOXIDE MT 150 W" from the company TAYCA.

There may also be mentioned the mixtures of metallic oxides, especially of titanium dioxide and cerium dioxide, including the equiponderal mixture of titanium dioxide and cerium dioxide, coated with silica, which is sold by the company IKEDA under the name "SUNVEIL A" as well as the mixture of titanium dioxide and zinc dioxide coated with alumina, silica and silicone, such as the product "M 261" sold by the company KEMIRA, or coated with alumina, silica and glycerin, such as the product "M 211" sold by the company KEMIRA.

The uncoated titanium oxides are for example sold by the company TAYCA under the trade names "MICROTITA-NIUM DIOXIDE MT 500 B" or "MICROTITANIUM DIOXIDE MT 600 B", by the company DEGUSSA under the name "P 25", by the company WACKHERR under the name "Transparent titanium oxide PW", by the company MIYOSHI KASEI under the name "UFTR" and by the company TOMEN under the name "ITS".

The uncoated zinc oxides are for example sold by the company SUMITOMO under the name "ULTRA FINE ZINC OXIDE POWDER", by the company PRESPERSE under the name "FINEX 25" or by the company IKEDA under the name "MZO-25".

The uncoated cerium oxide is sold under the name "COLLOIDAL CERIUM OXIDE" by the company RHONE POULENC.

The iron oxides are for example sold by the company HILTON DAVIS under the names "PUROXY YELLOW HIGH TRANSPARENCY", "PURE OXY RED HIGH TRANSPARENCY" and "PUROXY BLACK HIGH TRANSPARENCY".

According to the invention, the coated or uncoated nanopigments of titanium oxide are particularly preferred.

The fat-soluble hydrocarbon chain-containing screening polymers used according to the invention may be:

a) polyethyleneimine, chitin or chitosan polymers with an optionally substituted polyethylenic structure on which are grafted ultraviolet radiation-absorbing molecules via an ester, amide, ether, thioether, sulfonyl or acyl functional group, b) polymers resulting from the homo- or copolymerization of ultraviolet radiation-absorbing molecules ("screening monomers") carrying an unsaturated group chosen from the radicals: allyl, vinyl, acrylamide, methacrylamide, vinyloxycarbonylmethyl, acrylamidoalkyl and especially acrylamidomethyl, methacrylamidoalkyl, acrylamido(phenyl)alkyl, methacrylamido(phenyl)alkyl, acryloyloxy, acryloyloxy-alkyl and acryloyloxypolyoxyethylene, optionally with other unsaturated monomers.

By way of ultraviolet radiation-absorbing molecules, the following compounds may be mentioned:

benzylidenecamphor and its derivatives substituted on the benzene nucleus, isophthalylidenecamphor and terephthalylidenecamphor, optionally substituted on the benzene nucleus, cinnamic acid, optionally substituted by one or more lower alkoxy groups and its esters, salicylic acid and its esters, benzoic acid and its esters, p-aminobenzoic acid and its derivatives which are alkylated on the amino group and their esters, optionally substituted hydroxybenzophenones, optionally substituted dibenzoylmethane, benzotriazole and 2-arylbenzotriazoles 2-arylbenzimidazoles, 2-arylbenzofurans, 2-arylbenzoxazoles, 2-arylindoles, mono- or diphenylcyanoacrylates, absorbers of coumarin structure.

By way of unsaturated monomers which are copolymerizable with the "screening monomers", there may be mentioned:

acrylic, methacrylic, itaconic and crotonic acids or their esters, acrylamide and its derivatives, methacrylamide and its derivatives, acrylonitrile, methacrylonitrile, styrene, α-methylstyrene, isoprene, butadiene, ethylene, propylene, vinyl esters, vinyl ethers, vinyl chlorides and fluorides, vinylidene chloride, N-vinylpyrrolidone, N-methacryloyl-D-glucosamine and monoesters and diesters of maleic and fumaric acids.

In the present invention, "fat-soluble polymer" is understood to mean a polymer which is insoluble in water at a concentration greater than 0.1% by weight, at room temperature, and which is soluble or dispersible in a cosmetic oil such as isopropyl adipate at a concentration of at least 1% by weight, at room temperature.

By way of fat-soluble hydrocarbon chain-containing screening polymers which can be used according to the invention, there may be mentioned by way of examples:

1) the polymers containing units of formula (I):

in which

Z denotes:

a) —CONHCH$_2$X, A denoting a hydrogen atom and X denoting a UV-absorbing aromatic group, such as those described in French Patents Nos. 2,597,336; 2,237,912; 2,359,857 and 2,596,400, in which X is preferably chosen from benzylidenecamphor radicals optionally substituted in positions 3 and 4 by a $C_1$–$C_{12}$ alkoxy radical or by a methylenedioxy radical, from 2-(2'-hydroxyphenyl) benzotriazole radicals optionally substituted in position 5' by a methyl or tert-octyl radical, from 4-methoxy-4'-tert-butyldibenzoylmethane radical, 4-hydroxybenzophenone radical, 2-hydroxybenzophenone radical optionally substituted by a methoxy group in position 4, from radicals derived from 4-hydroxycoumarin and 7-hydroxycoumarin;

b) 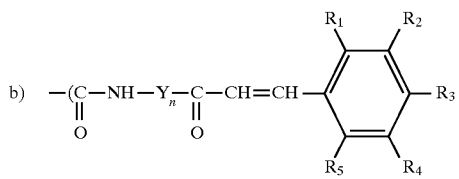

where n is 0 or 1
when n=0, A represents a hydrogen atom;
when n=1, A represents a hydrogen atom or a methyl radical,
$R_1$, $R_2$, $R_3$, $R_4$ and $R_5$, which are identical or different, represent a hydrogen atom, a linear or branched alkyl radical having 1 to 8 carbon atoms, an alkoxy radical having 1 to 4 carbon atoms, a dialkylamino radical or a dialkylaminoalkyl radical of formula

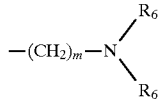

in which m is 1 to 3 and $R_6$ represents a methyl or ethyl radical, the said radicals being optionally quaternized by means of a quaternizing agent chosen from the group consisting of methyl chloride, dodecyl bromide, dimethyl sulfate and chloroacetic acid;
Y being zero or being capable of denoting —$CH_2$—, —CH($CH_3$)—,

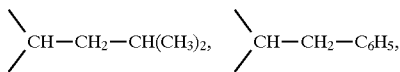

—C($CH_3$)$_2$—$CH_2$—, these polymers being described in French Patent No. 2,617,399;

2) the polymers derived from vinyl acetate containing the unit of formula (II)

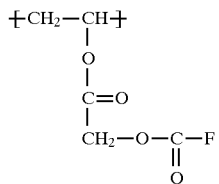 (II)

in which F represents a UV-absorbing radical such as those described in French Patents Nos. 2,197,023 and 2,359,856;
the group

being preferably chosen from a ($C_1$–$C_4$ p-dialkyl) aminobenzoate group, a cinnamate group which is optionally substituted by a methoxy, a salicylate group, a diphenylcyanoacrylate group and a flufenate or 3'-trifluoromethyldiphenylamine-2-carboxylate group;

3) the copolymers of polyethyleneimine with a molecular weight of between 500 and 100,000 and ($C_1$–$C_4$ para-dialkyl)aminobenzoic acid chloride, such as those described in U.S. Pat. No. 3,864,473;

4) the copolymers of monomers with ethylenic unsaturations and 4-(N,N-diallylamino)benzoic acid derivatives or its esters, such as those described in U.S. Pat. No. 3,795,733;

5) the polymerization products of the monomers of formula

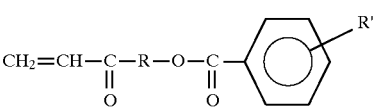

in which
R denotes —(X)$_n$—O— or —(CH$_2$CH$_2$—O)$_n$—,
X denoting a divalent alkylene, arylene or alkylarylene radical,
n=1 to 1000,
R' denotes OH, N(R$_1$)$_2$,
R$_1$ denotes H, alkyl, aryl or alkylaryl,
the alkyl radicals having 1 to 20 carbon atoms, such as those described for example in Patent WO 88/09783;

6) the polymers derived from chitin and chitosan carrying at least one UV-absorbing group of formula:

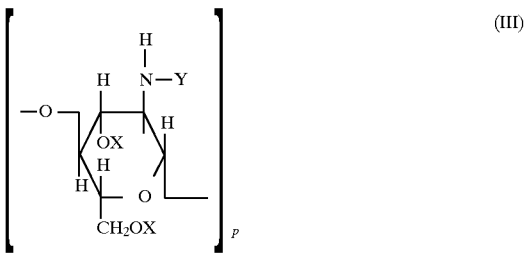 (III)

in which:
X and Y, independently of each other, denote hydrogen, a benzoyl radical of formula (IV) or a cinnamoyl radical of formula (V) and Y may also denote acetyl:

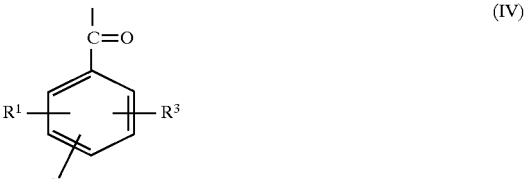 (IV)

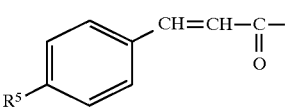 (V)

in which formulae:
$R^1$, $R^2$ and $R^3$, which are identical or different, denote hydrogen, $C_1$–$C_4$ alkoxy, hydroxy or

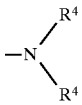

$R^4$ denoting hydrogen, $C_1$–$C_4$ alkyl, $C_2$–$C_4$ monohydroxyalkyl or $C_2$–$C_4$ dihydroxy alkyl, provided that at least one of the groups $R^1$, $R^2$ or $R^3$ does not denote hydrogen and that at most one of the groups $R^1$, $R^2$ or $R^3$ denotes

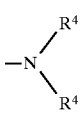

$R^5$ denotes $C_1$–$C_4$ alkoxy p=3–20,000,
provided that when X denotes hydrogen, Y denotes neither hydrogen nor acetyl;

such polymers are described in German Patent Application No. 3,912,122.

The preferred hydrocarbon chain-containing fat-soluble screening polymers according to the invention are polyacrylamides with optionally substituted benzylidenecamphor graft units X as defined above in 1)a).

The siloxane chain-containing screening polymers used according to the invention are diorganopolysiloxanes containing in their molecule at least one unit of formula:

in which

R' denotes a saturated or unsaturated $C_1$–$C_{30}$ hydrocarbon group, a halogenated $C_1$–$C_8$ hydrocarbon group or a trimethylsilyloxy group;

a=1 or 2;

X=—A—Y where A represents a divalent aliphatic or aromatic hydrocarbon radical containing at least 2 carbon atoms and optionally containing one or more oxygen atoms;

Y represents the residue of an ultraviolet radiation-screening molecule.

In addition to the units of formula (VI), the diorganopolysiloxane may contain units of formulae:

and

in which

R' and a have the same meaning as in formula (VI);

b is an integer denoting 1, 2 or 3;

Z=—O—Y, Y having the same meaning as in formula (VI).

By way of hydrocarbon group, there may be mentioned a $C_1$–$C_{30}$ alkyl radical, a $C_2$–$C_{30}$ alkenyl radical, a cycloalkyl or aromatic radical such as a phenyl or tolyl radical.

By way of halogenated hydrocarbon group, there may be mentioned a 3,3,3-trifluoropropyl radical.

In the diorganopolysiloxane consisting of (VI), and optionally (VII) and (VIII), units, at least 40% in numerical terms of the R' radicals are methyl radicals. The total number of (VI), (VII) and (VIII) units is preferably less than or equal to 250 and is in particular between 2 and 50.

Y preferably represents:
a benzylidenecamphor residue which is optionally substituted on the benzene nucleus by hydroxyl, alkyl or $C_1$–$C_6$ alkoxy radicals;
a $C_1$–$C_8$ dialkyl benzalmalonate residue which is optionally substituted on the benzene nucleus by hydroxy, alkyl or $C_1$–$C_6$ alkoxy radicals;
a 2-(2'-hydroxyphenyl)benzotriazole residue optionally carrying on one of the aromatic nuclei $C_1$–$C_8$ alkyl or $C_2$–$C_8$ alkenyl, halogen, alkoxy, carboxy, hydroxy, amino or tetraalkylpiperidyl substituents;
a dibenzoylmethane residue optionally carrying $C_1$–$C_8$ alkyl or alkoxy or hydroxy substituents;
a benzophenone residue optionally carrying $C_1$–$C_8$ alkyl or alkoxy or hydroxy substituents;
a benzoate residue substituted by hydroxy, $C_1$–$C_6$ alkoxy, amino or mono- or di-($C_1$–$C_6$ alkyl)amino radicals.

Such siloxane chain-containing screening polymers are described in European Patent Applications Nos. 0,335,777; 0,392,882; 0,388,218; 0,392,883; 0,383,655 and 0,389,337 and in French Patents 2,550,787 and 2,657,351 and in American patents U.S. Pat. Nos. 4,696,969; 4,554,369; 4,562,278; 3,513,184 and 4,859,759.

The screening silicones preferred for use according to the invention are those in which the radical Y denotes a benzylidenecamphor radical or an optionally substituted 2-(2'-hydroxyphenyl)benzotriazole radical as defined above.

The concentration of nanopigments in the compositions according to the invention is between 0.1 and 15% by weight and preferably between 0.5 and 10% by weight relative to the total weight of the composition.

The screening polymer(s) are present at a total concentration of between 0.1 and 15% by weight and preferably between 0.5 and 10% by weight relative to the total weight of the composition.

The nanopigment(s)/screening polymer(s) ratio by weight is advantageously between 0.1 and 10 and preferably between 0.5 and 5.

The cosmetic composition of the invention may be used as composition for protecting the human epidermis or the hair against ultraviolet rays, as an anti-sun composition or as a make-up product.

This composition may be provided in particular in the form of a lotion, a thickened lotion, a gel, an oil, a vesicular dispersion, a cream, a milk, a powder or a solid stick and may optionally be packaged as an aerosol and provided in the form of a foam or a spray.

It may contain the cosmetic adjuvants generally used, such as fatty substances, organic solvents, silicones, thickeners, emollients, UV-A, UV-B or broad band sunscreen agents, antifoaming agents, moisturizing agents, perfumes, preservatives, surfactants, fillers, sequestrants, anionic, cationic, nonionic and amphoteric polymers or mixtures thereof, propellants, alkalinizing or acidifying agents, colorants, pigments of metallic oxides with a particle size of between 100 nm and 20,000 nm such as iron oxides, or any other ingredient generally used in the cosmetic field.

The fatty substances may consist of an oil or a wax or a mixture thereof, fatty acids, fatty alcohols, vaseline, paraffin, lanolin, hydrogenated lanolin or acetylated lanolin.

The oils are chosen from animal, vegetable, mineral or synthetic oils and especially hydrogenated palm oil, hydrogenated castor oil, vaseline oil, paraffin oil, Purcellin oil, silicone oils and isoparaffins.

The waxes are chosen from animal, fossile, vegetable, mineral or synthetic waxes. There may be mentioned especially beeswaxes, Carnauba wax, Candelilla wax, sugar cane wax, Japan wax, ozokerites, Montan wax, microcrystalline waxes, paraffins, silicone waxes and resins.

When the cosmetic composition according to the invention is used for protecting the human epidermis against UV rays, or as an anti-sun composition, it may be provided in the form of a suspension or a dispersion in solvents or fatty substances, or alternatively in the form of an emulsion such as a cream or a milk, in the form of an ointment, a gel, a solid stick or an aerosol foam.

The emulsions may contain, in addition, anionic, nonionic, cationic or amphoteric surface-active agents.

It may also be provided in the form of a vesicular dispersion of ionic or nonionic amphiphilic lipids which is prepared according to known processes. The lipids may for example be swollen in an aqueous solution to form spherules dispersed in the aqueous medium as described in the publication BANGHAM, STANDISH & WATKINS, J. Mol. Biol., 13, 238 (1965) or in Patents FR-2,315,991 and 2,416,008 by the Applicant.

When the cosmetic composition according to the invention is used for protecting the hair, it may be provided in the form of a rinse-off shampoo, lotion, gel or composition to be applied before or after shampooing, before or after dyeing or bleaching, before, during or after permenent waving or hair straightening, a hair styling or treatment lotion or gel, a lotion or gel for blow drying or hair setting, a hair lacquer, a composition for permanent waving or hair straightening, and for dyeing or bleaching the hair.

When the composition is used as a make-up product for the eyelashes, eyebrows or the skin, such as a cream for treating the epidermis, a foundation, a lipstick, an eyeshadow, a blusher, a mascara or an eye liner, it may be provided in solid or pasty, anhydrous or aqueous form, such as oil-in-water or water-in-oil emulsions, vesicular dispersions or alternatively suspensions.

The subject of the invention is also a process for protecting the human epidermis and the hair against ultraviolet radiation, consisting in applying to the skin or the hair an effective quantity of the above cosmetic composition.

The invention will be illustrated more clearly by the nonlimiting examples below.

EXAMPLE 1

An anti-sun cream of the following composition is prepared:

Titanium oxide coated with iron oxide and iron stearate (mean diameter 15 nm) sold under the name "MICROTITANIUM DIOXIDE MT 100 F" by the company TAYCA 5 g Polydimethylsiloxane containing a 2-(3'-trimethylene-5'-methyl-2'-hydroxyphenyl)benzotriazole graft unit of formula: 5 g

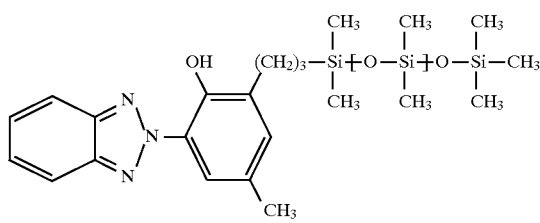

according to Example 1 of Application EP 0,388,218

| | |
|---|---|
| Mixture of glycerol stearate and polyethylene glycol stearate containing 100 moles of ethylene oxide sold under the name "Arlacel 165" by the company ICI | 1 g |
| Isostearic acid | 2 g |
| 2-Octyldodecanol | 15 g |
| Stearyl alcohol | 1 g |
| Glycerin | 3 g |
| Sorbitol in aqueous solution at 70% AI | 1.4 g AI |
| Cross-linked polyacrylic acid sold under the name "CARBOPOL 940" by the company GOODRICH | 0.3 g |
| Triethanolamine | 0.4 g |
| Preservatives, antioxidant | qs |
| Perfume | qs |
| Water | qs 100 g |

EXAMPLE 2

An anti-sun cream of the following composition is prepared:

| | |
|---|---|
| Titanium oxide coated with iron oxide and iron stearate (mean diameter 15 nm) sold under the name "MICROTITANIUM DIOXIDE MT 100 F" by the company TAYCA | 5 g |
| Poly(4'-acrylamidomethyl-3-benzylidenecamphor) of Example 1 of French Patent No. 2,597,336 consisting of the units: | 5 g |

$$\left[ \begin{array}{c} CH_2-CH \\ | \\ CO \\ | \\ NH-CH_2- \end{array} \right]$$

| | |
|---|---|
| Mixture of glycerol stearate and polyethylene glycol stearate containing 100 moles of ethylene oxide sold under the name "ARLACEL 165" by the company ICI | 1 g |
| Isostearic acid | 2 g |
| 2-Octyldodecanol | 15 g |
| Stearyl alcohol | 1 g |
| Glycerin | 3 g |
| Sorbitol in aqueous solution at 70% AI | 1.4 g AI |
| Cross-linked polyacrylic acid sold under the name "CARBOPOL 940" by the company GOODRICH | 0.3 g |
| Triethanolamine | 0.4 g |
| Preservatives, antioxidant qs | |
| Perfume qs | |
| Water qs | 100 g |

EXAMPLE 3

An anti-sun O/W emulsion of the following composition is prepared:

| | |
|---|---|
| Mixture of glycerol stearate and polyethylene glycol stearate containing 100 moles of ethylene oxide sold under the name "ARLACEL 165" by the company ICI | 2 g |
| Vaseline oil | 8 g |

-continued

| | |
|---|---|
| Stearic acid | 2 g |
| Lanolin | 2 g |
| Stearyl alcohol | 1 g |
| Polydimethylsiloxane containing 2-(3'-trimethylene-2'-hydroxy-5'-methylphenyl)-benzotriazole graft units according to Application EP 0,392,883 | 2 g |

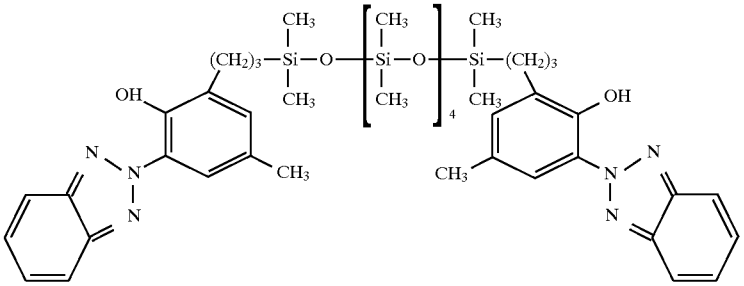

| | |
|---|---|
| Glycerin | 3 g |
| Sorbitol in aqueous solution at 70% AI | 1.4 g AI |
| Hydroxyethyl cellulose modified by a cetyl chain sold under the name "NATROSOL PLUS GRADE 336 CS" by the company AQUALON | 0.5 g |
| Potassium hexadecylphosphate | 0.5 g |
| Sodium acetate monohydrate | 0.2 g |
| Colloidal cerium oxide sold in aqueous solution at 20% AI by the company RHONE POULENC under the name "COLLOIDAL CERIUM OXIDE" | 2 g AI |
| Preservatives qs | |
| Water qs | 100 g |

EXAMPLE 4

An anti-sun O/W emulsion of the following composition is prepared:

| | |
|---|---|
| Mixture of glycerol stearate and polyethylene glycol stearate containing 100 moles of ethylene oxide sold under the name "ARLACEL 165" by the company ICI | 2 g |
| Vaseline oil | 8 g |
| Stearic acid | 2 g |
| Lanolin | 2 g |
| Stearyl alcohol | 1 g |
| Mixture of polydimethylsiloxanes containing 4'-trimethyleneoxy-3-benzylidenecamphor and 4'-oxy-3-benzylidenecamphor graft units, which is prepared according to Application EP 0,335,777, and having the formula: $$CH_3-Si(CH_3)_2-O-[Si(CH_3)_2-O]_x-[Si(CH_3)((CH_2)_3 OBC)-O]_y-[Si(CH_3)(OBC)-O]_z-Si(CH_3)_3$$ consisting of about: 55% polydimethylsiloxane. in which $x = 0$ to 20, $y = 1$ to 4, $z = 0$ 5% polydimethylsiloxane in which $x = 0$ to 21, $y = 0$, $z = 1$ to 4 40% polydimethylsiloxane in which $x = 0$ to 16, $y = 1$ to 3, $z = 1$ to 3, BC denoting the 3-benzylidenecamphor radical | 2 g |
| Glycerin | 3 g |
| Sorbitol in aqueous solution at 70% AI | 1.4 g AI |

| | |
|---|---|
| Hydroxyethyl cellulose modified by a cetyl chain sold under the name "NATROSOL PLUS GRADE 330 CS" by the company AQUALON | 0.5 g |
| Potassium hexadecylphosphate | 0.5 g |
| Sodium acetate monohydrate | 0.2 g |
| Titanium oxide coated with iron oxide and iron stearate (mean diameter 15 nm) sold under the name "MICROTITANIUM DIOXIDE MT 100 F" by the company TAYCA | 2.5 g |
| Preservatives qs | |
| Water qs | 100 g |

EXAMPLE 5

An anti-sun O/W emulsion of the following composition is prepared:

| | |
|---|---|
| Mixture of glycerol stearate and polyethylene glycol stearate containing 100 moles of ethylene oxide sold under the name "ARLACEL 165" by the company ICI | 2 g |
| Vaseline oil | 8 g |
| Stearic acid | 2 g |
| Lanolin | 2 g |
| Stearyl alcohol | 1 g |
| Graft polydimethylsiloxane derived from benzophenone of formula: | 2 g |

$$\begin{array}{c} CH_3 \quad CH_3 \quad CH_3 \\ | \quad\quad | \quad\quad | \\ CH_3-Si-O-Si-O-Si-CH_3 \\ | \quad\quad | \quad\quad | \\ CH_3 \quad CH_2 \quad CH_3 \\ \quad\quad | \\ \quad\quad CH_2 \\ \quad\quad\quad \diagdown CH_2 \end{array}$$

(attached to a 2-hydroxy-4-methoxybenzophenone group)

| | |
|---|---|
| Glycerin | 3 g |
| Sorbitol in aqueous solution at 70% AI | 1.4 g AI |
| Hydroxyethyl cellulose modified by a cetyl chain sold under the name "NATROSOL PLUS GRADE 330 CS" by the company AQUALON | 0.5 g |
| Potassium hexadecylphosphate | 0.5 g |
| Sodium acetate monohydrate | 0.2 g |
| Zinc oxide sold under the name "ULTRA FINE ZINC OXIDE POWDER" by the company SUMITOMO | 2 g |
| Preservatives qs | |
| Water qs | 100 g |

EXAMPLE 6

A cream gel of the following composition is prepared:

| | |
|---|---|
| Glycerin | 3 g |
| Vaseline oil | 5 g |
| Oil-in-water emulsion of cross-linked acrylamido/sodium 2-acrylamido-2-methylpropanesulfonate copolymer, sold by the company SEPPIC under the name "SEPIGEL 305" with 40% AI in copolymer | 1.2 g AI in copolymer |
| Titanium oxide coated with iron oxide and iron stearate (mean diameter 15 nm) sold under the name "MICROTITANIUM | 1.33 g |

-continued

| DIOXIDE MT 100 F" by the company TAYCA Graft polydimethylsiloxane derived from benzophenone of formula: | 2.67 g |
|---|---|

$$CH_3-\underset{\underset{CH_3}{|}}{\overset{\overset{CH_3}{|}}{Si}}\!+\!O\!-\!\underset{\underset{CH_3}{|}}{\overset{\overset{CH_3}{|}}{Si}}\!+\!_{\overline{15}}O\!-\!\underset{\underset{CH_3}{|}}{\overset{\overset{CH_3}{|}}{Si}}\!-\!CH_2\!-\!CH_2\!-\!CH_2\!-\!\underset{CH_3O}{\underset{|}{\bigcirc}}\!\underset{OH}{\overset{}{\bigcirc}}\!-\!\overset{O}{\overset{||}{C}}\!-\!\bigcirc$$

| according to French Patent Application. FR 2,657,351 | |
|---|---|
| Mixture of dimethiconol (13%), octa-methylcyclotetrasiloxane and decamethyl-cyclopentasiloxane (87%), sold under the name "Q2-1401" by the company DOW CORNING | 5 g |
| Methyl polymethacrylate powder (15μ) sold under the name "MICROPEARL M 100" by the company SEPPIC | 3 g |
| Preservatives qs | |
| Water qs | 100 g |

We claim:

1. A screening cosmetic composition, comprising, in a cosmetically acceptable carrier, at least one coated nanopigment of metallic oxides selected from the group consisting of titanium, zinc, cerium, zirconium and iron oxides and mixtures thereof, with a mean diameter of less than 100 nm, having undergone one or more surface treatments of a chemical, electronic, mechanicochemical or mechanical nature with compounds selected from the group consisting of amino acids, beeswax, fatty acids, fatty alcohols, anionic surfactants, lecithins, sodium, potassium, zinc, iron and aluminum salts of fatty acids, metallic alkoxides, polyethylene, silicones, proteins, alkanolamines, silicon oxides, metallic oxides and sodium hexametaphosphate, and at least one polymer with a siloxane structure carrying at least one ultraviolet-absorbing group, said polymer with the siloxane structure consisting of diorganopolysiloxane containing in their molecule at least one unit of formula:

$$X-\underset{\underset{}{|}}{\overset{\overset{R'_a}{|}}{Si}}-O_{\frac{3-a}{2}} \qquad (VI)$$

in which:

R' denotes a saturated or unsaturated $C_1$–$C_{30}$ hydrocarbon group, a halogenated $C_1$–$C_8$ hydrocarbon group or a trimethylsilyloxy group;

a=1 or 2;

X=—A—Y where A represents a divalent aliphatic or aromatic hydrocarbon radical containing at least 2 carbon atoms and optionally containing one or more oxygen atoms, and Y represents the residue of an ultraviolet radiation-screening molecule which is a benzylidenecamphor residue which is unsubstituted or substituted on the benzene nucleus by a hydroxyl, $C_1$–$C_6$ alkyl or alkoxy radical; a $C_1$–$C_8$ dialkyl benzalmalonate residue which is unsubstituted or substituted on the benzene nucleus by hydroxyl, $C_1$–$C_6$ alkyl or alkoxy radicals; a 2-(2'-hydroxyphenyl)benzotriazole residue which is unsubstituted or carrying on one of the aromatic nuclei $C_1$–$C_8$ alkyl, $C_2$–$C_8$ alkenyl, halogen, alkoxy, carboxy, hydroxy or amino substituents; a dibenzoylmethane residue which is unsubstituted or carrying $C_1$–$C_8$ alkyl or alkoxy or hydroxy substituents; or a benzoate residue which is substituted by hydroxy, $C_1$–$C_8$ alkoxy, amino or mono- or di($C_1$–$C_6$ alkyl)amino radicals.

2. Cosmetic composition according to claim 1, wherein the nanopigments of metallic oxides have a diameter of between 5 and 50 nm.

3. Cosmetic composition according to claim 1, wherein the metallic oxide is titanium oxide.

4. Cosmetic composition according to claim 1, wherein the coated nanopigment of metallic oxides is a pigment of titanium oxide coated with silica, with silica and alumina, with silica and iron oxide, with alumina and silicone, with alumina, with alumina and aluminum stearate, with alumina and aluminum laurate, with iron oxide and iron stearate, with zinc oxide and zinc stearate, with silica and alumina and silicone, with silica and alumina and aluminum stearate and silicone, with triethanolamine, with stearic acid or with sodium hexametaphosphate.

5. Cosmetic composition according to claim 1, which contains 0.1 to 15% by weight relative to the total weight of the composition, of at least one nanopigment of metallic oxides.

6. Cosmetic composition according to claim 1, wherein the diorganopolysiloxane contains, in addition, units having the formulae:

$$R'_b-SiO_{\frac{4-b}{2}} \qquad (VII)$$

and $$Z-\underset{\underset{}{|}}{\overset{\overset{R'_a}{|}}{Si}}-O_{\frac{3-a}{2}} \qquad (VIII)$$

in which R' and a have the meanings indicated in claim 1, b is an integer equal to 1, 2 or 3, Z=—O—Y, Y having the same meaning as in claim 1, at least 40% in numerical terms of the R' radicals denoting methyl.

7. Cosmetic composition according to claim 1, which comprises a polydimethylsiloxane with 2-(3'-trimethylene-5'-methyl-2'-hydroxyphenyl)benzotriazole graft unit(s).

8. Cosmetic composition according to claim 1, which comprises a mixture of polydimethylsiloxanes with 4'-trimethyleneoxy-3-benzylidenecamphor and 4'-oxy-3-benzylidenecamphor graft units.

9. Cosmetic composition according to claim 1, which contains 0.1 to 15% by weight, relative to the total weight of the composition, of at least one fat-soluble screening polymer with hydrocarbon or siloxane structure.

10. Cosmetic composition according to claim 1, wherein the nanopigment(s)/screening polymer(s) ratio by weight is between 0.1 and 10.

11. Cosmetic composition according to claim 1, which constitutes a composition for protecting the human epidermis or an anti-sun composition and is provided in the form of a lotion, a thickened lotion, a gel, an oil, a vesicular dispersion, a cream, a milk, a powder, a solid stick, a foam or a spray.

12. Cosmetic composition according to claim 1, which constitutes a make-up composition for the eyelashes, eyebrows or skin and is in solid or pasty, anhydrous or aqueous form, as emulsion, suspension or vesicular dispersion.

13. Cosmetic compositin according to claim 1, which is used for protecting the hair against ultraviolet rays, which is in the form of a rinse-off shampoo, lotion, gel or composition to be applied before or after shampooing, before or after dyeing or bleaching, before, during or after permenent waving or hair straightening, a hair styling or treatment lotion or gel, a lotion or gel for blow drying or hair setting, a hair lacquer, a composition for permanent waving or hair straightening, and for dyeing or bleaching the hair.

14. Cosmetic composition according to claim 1, which comprises, in addition, cosmetic adjuvants selected from the group consisting of fatty substances, organic solvents, silicones, thickeners, emollients, UV-A, UV-B and broad band sunscreen agents, antifoaming agents, moisturizing agents, perfumes, preservatives, surfactants, fillers, sequestrants, anionic, cationic, nonionic and amphoteric polymers and mixtures thereof, propellants, alkalinizing and acidifying agents, colorants, and pigments of metallic oxides with a particle size of between 100 nm and 20,000 nm.

15. Process for protecting the human epidermis and the hair against ultraviolet radiation of wavelengths of between 280 and 400 nm, consisting in applying to the skin or the hair an effective quantity of a cosmetic composition according to any one of claims 1 to 14.

* * * * *